United States Patent [19]

Hösel

[11] Patent Number: 4,962,569
[45] Date of Patent: Oct. 16, 1990

[54] METHOD AND APPARATUS FOR OBTAINING MEASURING VALUES REPRESENTING THE THICKNESS OF A COHERENT FIBER MASS

[75] Inventor: Fritz Hösel, Mönchengladbach, Fed. Rep. of Germany

[73] Assignee: Trüzschler GmbH & Co. KG, Mönchengladbach, Fed. Rep. of Germany

[21] Appl. No.: 306,308

[22] Filed: Feb. 3, 1989

[30] Foreign Application Priority Data

Feb. 5, 1988 [DE] Fed. Rep. of Germany ....... 3803353

[51] Int. Cl.$^5$ .......................................... D01G 15/46
[52] U.S. Cl. ................................. 19/106 R; 19/0.23
[58] Field of Search ............... 19/105, 106 R; 73/159, 73/160; 250/211 R; 377/6

[56] References Cited

U.S. PATENT DOCUMENTS

| | | | |
|---|---|---|---|
| 2,037,191 | 9/1932 | Backer | 377/6 |
| 3,157,915 | 7/1959 | Gilbo | 19/106 R |
| 3,562,866 | 10/1968 | Roberson et al. | 19/105 |
| 3,652,864 | 3/1972 | Person | 377/6 |
| 3,737,856 | 6/1973 | Lehrer et al. | 377/6 |
| 4,040,092 | 8/1977 | Carnes | 250/211 R |
| 4,271,565 | 6/1981 | Grunder | 19/105 |
| 4,272,868 | 6/1981 | Grunder et al. | 19/105 |
| 4,635,215 | 1/1987 | Friend | 377/6 |
| 4,648,054 | 3/1987 | Farah et al. | 73/160 |
| 4,716,764 | 1/1988 | Felix | 73/160 |
| 4,779,310 | 10/1988 | Leifeld | 19/105 |
| 4,791,706 | 12/1988 | Wiening et al. | 19/105 |

FOREIGN PATENT DOCUMENTS

| | | |
|---|---|---|
| 205377 | 12/1986 | European Pat. Off. . |
| 1218324 | 12/1966 | Fed. Rep. of Germany . |
| 1952829 | 4/1970 | Fed. Rep. of Germany . |
| 1685563 | 3/1972 | Fed. Rep. of Germany . |
| 2140939 | 3/1973 | Fed. Rep. of Germany . |
| 2244433 | 3/1974 | Fed. Rep. of Germany . |
| 2448651 | 4/1975 | Fed. Rep. of Germany . |
| 2448611 | 11/1976 | Fed. Rep. of Germany . |
| 2741401 | 3/1978 | Fed. Rep. of Germany . |
| 3129890 | 6/1982 | Fed. Rep. of Germany . |
| 2948510 | 3/1983 | Fed. Rep. of Germany . |
| 3234330 | 4/1983 | Fed. Rep. of Germany . |
| 3239162 | 5/1983 | Fed. Rep. of Germany . |
| 3311345 | 2/1986 | Fed. Rep. of Germany . |
| 3034778 | 4/1986 | Fed. Rep. of Germany . |
| 3413420 | 6/1986 | Fed. Rep. of Germany . |
| 3536892 | 4/1987 | Fed. Rep. of Germany . |
| 3635267 | 5/1987 | Fed. Rep. of Germany . |
| 3641816 | 6/1988 | Fed. Rep. of Germany . |

Primary Examiner—4
Assistant Examiner—Michael A. Neas
Attorney, Agent, or Firm—Spencer & Frank

[57] ABSTRACT

An apparatus for generating measuring values representing the thickness of a coherent fiber material, includes an optical device having a light transmitter emitting a light beam and a light detector, an arrangement for guiding the fiber material between the light transmitter and the light detector and a device for processing signals generated by the light detector. The light detector comprises an image processing CCD member aligned with the light beam emitted by the light transmitter.

20 Claims, 9 Drawing Sheets

METHOD AND APPARATUS FOR OBTAINING MEASURING VALUES REPRESENTING THE THICKNESS OF A COHERENT FIBER MASS

CROSS REFERENCE TO RELATED APPLICATION

This application claims the priority of Federal Republic of Germany Application No. P 38 03 353.4 filed Feb. 5, 1988, which is incorporated herein by reference.

BACKGROUND OF THE INVENTION

This invention relates to a method and apparatus for obtaining measuring values which represent the thickness of a coherent fiber mass, particularly a sliver discharged by a carding machine or the like. The apparatus is of the type which utilizes an optical device comprising at least one light transmitter and at least one light detector between which the coherent fiber mass is passed.

In the field of textile fabric making, particularly in the spinning or spinning preparation processes it is frequently necessary to determine the thickness of slivers discharged by cards or drawing frames and to apply the measuring values to regulators. For determining the thickness of the fiber material, various principles are used such as capacitive, mechanical, pneumatic and sonic sensing. All known thickness determining apparatuses used so far have the disadvantage that their range of application is limited. Thus, according to a known apparatus, a light source (stroboscope) and a light detector (photocell/photodiode) are used for measuring the density of the material. In this apparatus the sliver passes through a tube in which diametrically opposite windows are provided. The high-intensity stroboscope irradiates with light pulses the fiber sliver which, being in overall contact with the tube, has a constant diameter. Dependent upon the density of the sliver, the intensity of the radiation varies. Thus, one part of the light rays is absorbed by the fibers and the light rays which are not absorbed by the fibers are measured by the detector. Such an apparatus is not adapted to measure the thickness of the sliver because, particularly in case of fiber slivers, the risks are high that an untrue thickness (diameter) is measured since it is based on the light which passes through the sliver. It is a further disadvantage that such a device is at least in part color-sensitive so that for fiber materials of a different color new reference and setting values have to be determined.

SUMMARY OF THE INVENTION

It is an object of the invention to provide a method and an apparatus of the above-outlined type from which the discussed disadvantages are eliminated, which ensures in particular an increased accuracy of measurement of the fiber sliver thickness, which may be universally used and which is furthermore operationally reliable.

This object and others to become apparent as the specification progresses, are accomplished by the invention, according to which, briefly stated, the optical device includes an image processing, charge-coupled (CCD) member as the light detector and a light emitter is situated opposite the light detector.

Thus, according to the invention, the coherent fiber mass is passed through an optical device formed of at least one CCD member as the light detector and at least one light source as the light transmitter. The light transmitters and the CCD members are arranged in such a manner that with each light source there is associated a CCD member by positioning it opposite the light source. The CCD member is a chargecoupled component composed of an integrated circuit which makes possible the collective transfer of a plurality of mutually delimited, freely shiftable charge bundles from one location of memory to the other within an analog shift register. An analog location of memory is obtained by forming potential waves underneath the control electrode of the shift register. Alternating pulses at the shift electrodes effect a shift of the charge bundles in each instance by one location of memory for every dual impulse cycle. The number of the charge carriers of one charge bundle corresponds in each instance to the sample of the optical input information.

The light transmitters emit light rays to the associated CCD member, each having up to several thousands of small individual light sensor elements. Each light sensor element transmits a single electric signal if it detects light. When, during operation, the sliver or similar coherent fiber mass is passed between the light transmitters and the light receivers (CCD members), only those light receiving elements generate a signal which are not in the shadow of the sliver. The thickness of the sliver can be directly derived from the sum of the light receiving elements in shadow. In this process the dimensions of the light receiving elements and their distance to one another are known.

If information from the light sensors is requested in a predetermined cycle, based on such interrogating frequency the distance between two measurements taken on a moving sliver can be determined. For example, for each 2½ mm of the sliver a new value may be determined at a sliver speed of 300 m/min. If the interrogating frequency is synchronized with the sliver speed it may be ensured that measurements on the running sliver will always be performed at the same space intervals.

The apparatus according to the invention is advantageously adapted for measuring sliver volume irregularities, for example, for the purpose of generating a spectrogram. Assuming as a starting point that a fiber sliver of a predetermined fiber material at a predetermined volume has a predetermined weight, and that the relationship of these three values with respect to one another is also fixed and is linear, then by virtue of an appropriate calibration the weight can be directly derived from the volume for the same fiber material. The apparatus according to the invention thus makes possible sliver weight determinations (sliver numbers) as well.

It is a further advantage of the invention that the measuring result is independent from the running speed of the sliver and further, the apparatus—since it has no moving parts—is entirely maintenance-free and thus has a very long service life and has no system-dependent natural oscillations. Further, no sliver thickness-dependent measuring member is needed; that is, a single member may be used for all thicknesses.

In the apparatus according to the invention preferably a large number (for example, 2,048) of light receiving elements is utilized. By virtue of the particular manner, arrangement and number of the light detectors, it is possible to obtain - an exact representational image of the fiber sliver whereby a measurement of high precision is achieved.

The light transmitter may be irradiated by a light source or the light source may itself be the light transmitter. Preferably, a light diode is used as the light source.

Preferably, the light sources are turned on and off in cadence with the interrogating signal. By virtue of the fact that the light sources are turned on and off according to a predetermined cycle, and the receivers are interrogated only during an "on-phase" (impulse operation), the risks of an interference with the measuring results by extraneous light are securely eliminated. Preferably, infrared light is utilized in the measuring process. For a more accurate measuring an arbitrarily large number of CCD members and light transmitters or light sources may be used. The light sources may be arranged circularly or polygonally with respect to one another. In front of the light detectors and light sources, expediently optical systems, for example, lenses may be used for parallelizing beams or forming bundles therefrom. In order to prevent mutual interferences, the light detectors and light transmitters which are offset by 90°, are preferably arranged behind one another, as viewed in the travelling direction of the material.

The invention also comprises a method for setting (calibrating and adjusting) the apparatus for obtaining measuring magnitudes in which a fiber sliver of predetermined length and predetermined thickness is passed through the optical measuring device. With this procedure an average thickness and an average volume is determined, the fiber sliver is weighed and thus the sliver weight per unit length is determined and value pairs (average volume and sliver weight per unit length) are applied as a setting curve to the optical measuring device.

The setting of the device according to the invention in such a process is simple and void of problems. A predetermined amount of sliver with a predetermined thickness is passed through the optical measuring device which determines automatically an average volume. The same sliver, whose length is known is subsequently weighed and the sliver weight per unit length is determined. This value then is applied to the optical measuring device. The same process is subsequently repeated for another sliver thickness.

Based on the two value pairs (sliver weight and average volume) a setting curve for the predetermined fiber material is generated. Such a setting curve has to be stored once for each fiber material to be processed so that in case of repetition, no further adjustment is necessary. The adjusting process has to be performed only once for each type of fiber material. By virtue of the setting curve, sliver weights other than those processed during setting are directly set and produced.

DESCRIPTION OF THE PREFERRED EMBODIMENTS

Figure 1:
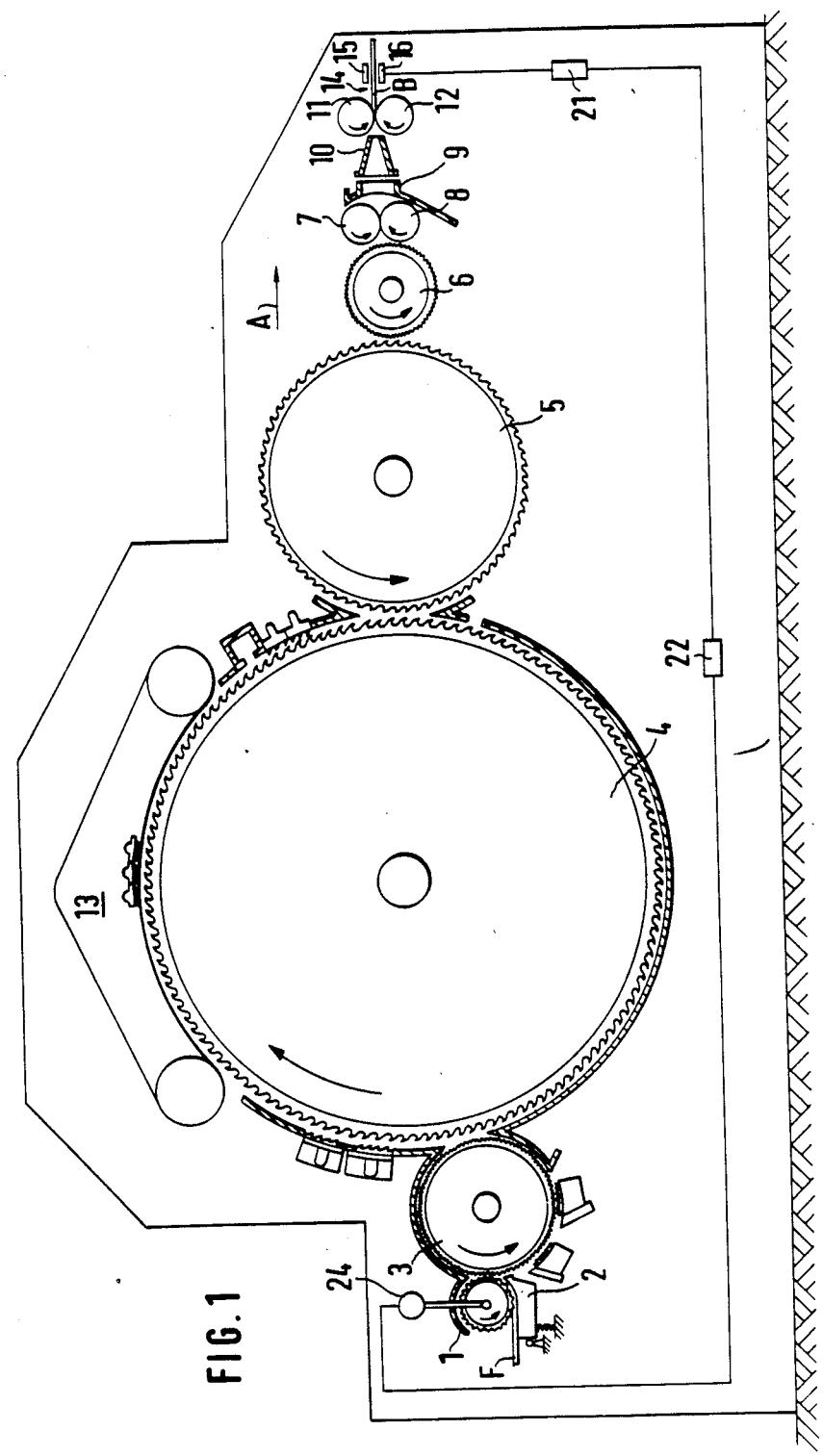
FIG. 1 is a schematic side elevational view of a carding machine incorporating the invention.

Turning to FIG. 1, there is shown therein a known carding machine which may be, for example, an EXACTACARD DK 740 model manufactured by Trützschler GmbH & Co. KG, Mönchengladbach, Federal Republic of Germany. The carding machine comprises a feed roller 1 cooperating with a feed table 2, a licker-in 3, a carding cylinder 4, a doffer 5, a stripping roller 6, crushing rollers 7, 8, a fiber web guide element 9, a sliver trumpet 10, calender rollers 11, 12 and travelling flats 13. The fiber material is supplied to the feed roller 1 as a fiber lap F, and the calender rollers 11, 12 discharge the fiber material as a fiber sliver B.

Figure 3:
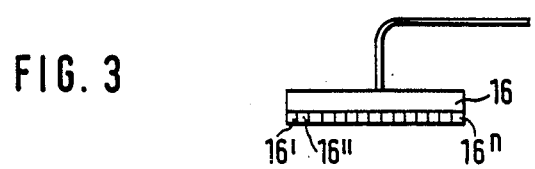
FIG. 3 is a schematic view of a CCD member with a plurality of light-receiving elements, forming part of the preferred embodiment of the invention.

Downstream of the calender rollers 11 and 12, as viewed in the direction of the advance of the fiber sliver B, there is arranged an optical device 14 according to the invention. The device comprises a light transmitter 15 and a light detector 16 situated thereacross. The light detector 16 comprises an image processing CCD member (charge-coupled device) which has a plurality of light detecting elements $16'$, $16''$ ... $16^n$ which are situated side-by-side as illustrated in FIG. 3. The width of the light detector 16 is greater than the diameter of the sliver B. A space is provided between the sliver B and the light detector 16 and between the sliver B and the light transmitter 15.

The CCD member may be an image processing CCD line sensor in which all photoelements are geometrically arranged in a precise line. The line sensor may be provided, for example, with 3,456 image dots (photoelements).

Since the CCD member as light sensor 16a, 16b is formed of, for example, 2,000 individual small light sensor elements $16'$, $16''$ ... $16^n$ which must all be interrogated linewise, and for the thickness determination the sum of the light detector elements are utilized, an interrogating cycle predetermined by the CCD member is automatically obtained.

Figure 2A:
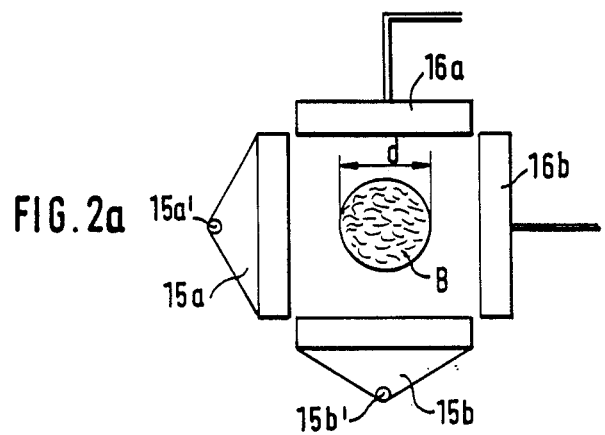
FIG. 2a is a schematic view illustrating two light transmitters and two light detectors at a 90° offset, forming part of a preferred embodiment of the apparatus according to the invention.
Figure 6:
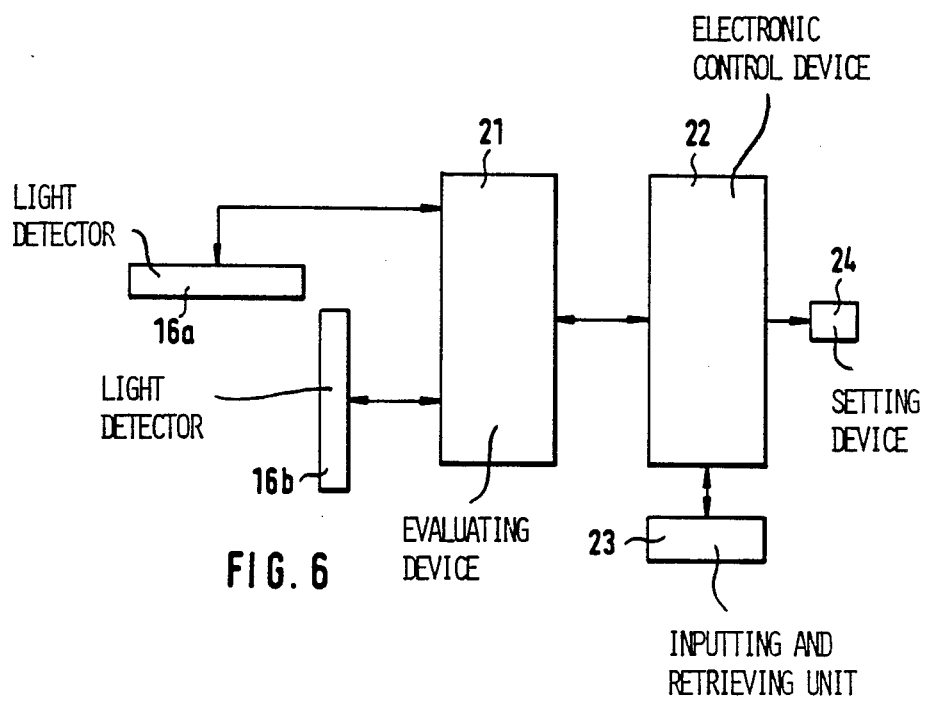
FIG. 6 is a block diagram of an electronic control and evaluating system of the preferred embodiment.

Turning now to FIG. 2a, the sliver B, having a diameter d, is passed through an annulus-like construction formed of two CCD light detectors 16a, 16b offset 90° and two light transmitters 15a, 15b also offset 90°. Each light transmitter 15a, 15b includes a respective light source $15a'$, $15b'$. The light transmitters 15a and 15b are situated opposite the respective light detector 16a and 16b. The latter are connected with an electronic control and evaluating device, as illustrated in FIG. 6.

Figure 2B:
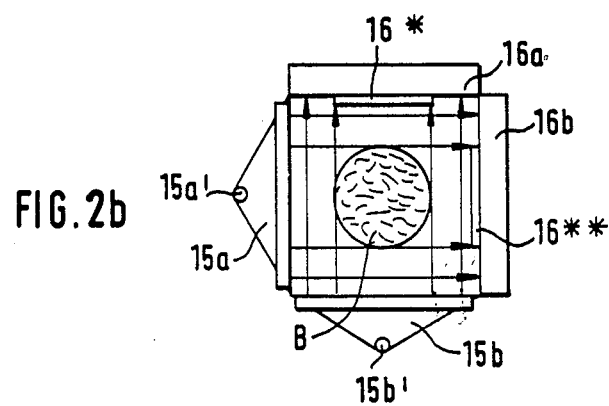
FIG. 2b is a view similar to FIG. 2a, illustrating the course of the light beams.

FIG. 2b illustrates how the light transmitters 15a and 15b direct the light beams towards the associated light detectors 16a and 16b. Each light detector 16a and 16b has up to several thousands of individual small light detector elements $16'$, $16''$ ... $16^n$, as shown in FIG. 3. Each element transmits only a single signal if light is detected. In case the fiber sliver B between the light transmitters 15a and 15b and the light detectors 16a and 16b is present, only those light detector elements 16', 16''. . . . 16$^n$ transmit an electric signal which is not situated in the shadow 16*, 16** of the sliver B. Based on the sum of the light detector elements 16', 16''. . . 16$^n$ situated in the shadows 16*, 16**, respectively, the thickness (or diameter) of the sliver may be directly derived.

Measuring in two directions, that is, in the direction of the two light detectors 16a, 16b has the advantage that deviations from a circular shape, for example, an elliptical or other cross section may be measured. Each of the individual small light detector elements 16', 16''. . . 16$^n$ has a light sensitive surface of a length of approximately 0.01 mm, and consequently, individual fibers which are thicker than 0.01 mm can be detected. For determining the sliver thickness, all non-illuminated light detecting elements 16', 16''. . . . 16$^n$ are added so that even boundary fibers (that is, fibers at the edge of the sliver) are counted. Since such a process step is the same for all slivers independently from the sliver thickness, a lack of sharpness at the edge of the sliver is inconsequential.

By virtue of the high resolution of the individual light sensor elements 16', 16'. . .16$^n$, it is feasible to generate and evaluate a detail-true image of the sliver B with the apparatus according to the invention. By virtue of the plurality of the performed measurements, a complete "movie" of the travelling sliver B is obtained.

The two light sensors 16a, 16b operate in a parallel manner. If the maximum interrogating frequency of the CCD members is utilized, a new thickness value may be obtained approximately every 2.5 mm of the running sliver B (assuming a running speed of 300 m/min).

Figure 2C:
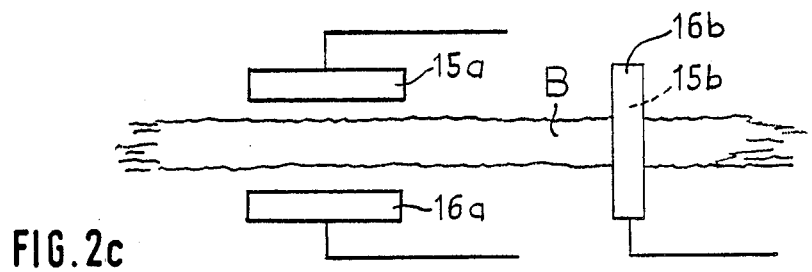
FIG. 2c is a schematic side elevational view of longitudinally spaced light sensor pairs forming part of a preferred embodiment of the apparatus according to the invention.

In order to prevent mutual interferences between the two detectors, FIG. 2c illustrates an embodiment wherein the two detectors 16a and 16b are not only offset by 90° angle with respect to one another but are also longitudinally spaced along the travelling path of the sliver B. The light transmitters 15a and 15b are similarly spaced and are thus in alignment with the respective light detectors 16a and 16b.

Figure 4:
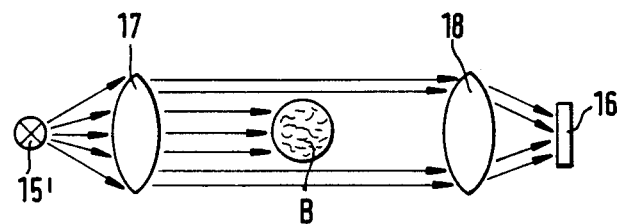
FIG. 4 is a schematic view of the optical sensor element according to the invention, including two lenses.

As shown in FIG. 4, the light source 15' is followed by an optical lens 17 and the detector 16 is preceded by an optical lens 18 such as a video camera. The sliver B is arranged at a distance between the oppositely located lenses 17 and 18.

Figure 5:
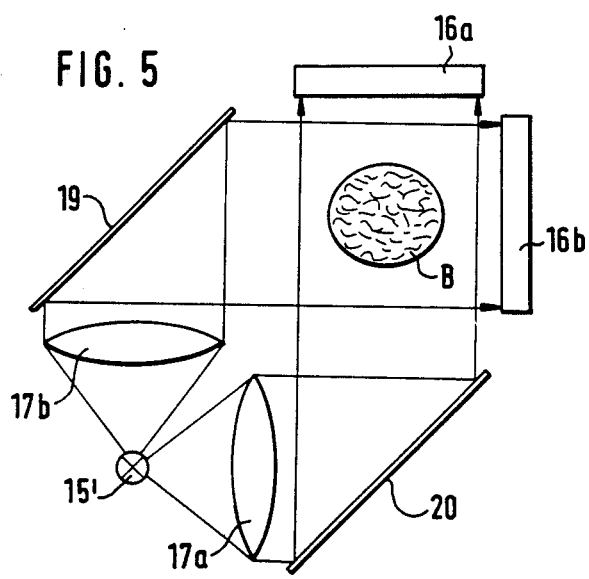
FIG. 5 is a schematic view of a further embodiment of the invention including a single light source and two light detectors.

Turning now to FIG. 5, there is illustrated therein an arrangement having a single light source 15' and two light detectors 16a and 16b. Between the lenses 17a and 17b arranged downstream of the light source 15' and the associated light detectors 16a and 16b there is arranged a reflecting element 19 and 20 such as a mirror. The sliver B has a slightly elliptical cross-sectional configuration.

Turning now to FIG. 6, the light detectors 16a and 16b are connected to an evaluating device 21, such as a microcomputer which may be a TMS model, manufactured by Trützschler GmbH & Co. KG. The evaluating device 21 is connected with an electronic control device 22, for example, for controlling the carding machine. To the control device 22 there is connected an inputting and retrieving unit 23. The control device 22 is connected with a setting device 24, for example, a regulatable drive motor 24 for the feed roller 1 of the carding machine.

Figure 7:
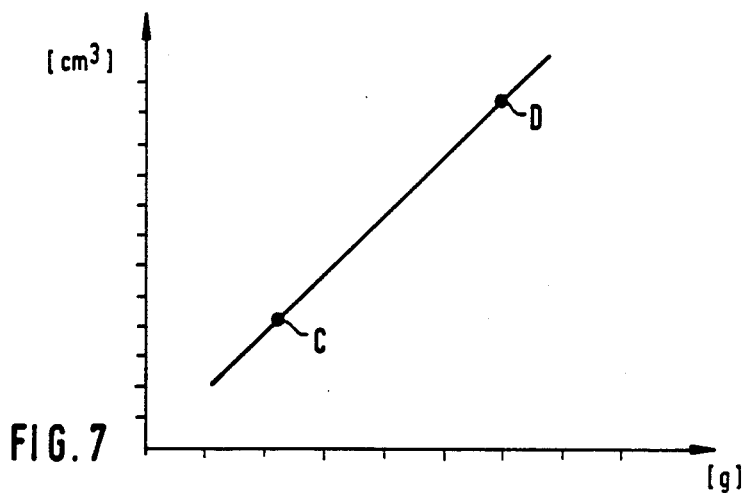
FIG. 7 is a diagram illustrating a setting curve representing the sliver weight as a function of the sliver volume.

FIG. 7 shows a setting curve which is obtained by the totality of value pairs C and D (sliver weight and average sliver volume).

In order to ensure a smooth run of the sliver B, it may be expedient to arrange a roller upstream and downstream of the optical device 14 for guiding the sliver B.

It may be further advantageous to utilize an optical fiber cable, to permit the light transmitters 15, 15a and 15b and/or the light detectors 16, 16a, 16b to be situated remote from the measuring location, whereby the available spaces may be advantageously utilized.

It will be understood that the above description of the present invention is susceptible to various modifications, changes and adaptations, and the same are intended to be comprehended within the meaning and range of equivalents of the appended claims.

What is claimed is:

1. In an apparatus for generating measuring values representing the thickness of a coherent fiber material, including an optical device having light transmitter means emitting alight beam and light detector means, means for guiding the fiber material between said light transmitter means and said light detector means and means for processing signals generated by said light detector; the improvement wherein said light detector means comprise first and second image processing CCD members and said light transmitter means comprise first and second light transmitters; said first and second CCD members being offset at an angle relative to one another and are aligned with the light beam of the first and the second light transmitter, respectively.

2. An apparatus as defined in claim 1, wherein said light transmitters and light detectors are disposed relative to one another such that they enclose a polygonal space through which the fiber material passes.

3. An apparatus as defined in claim 1, wherein said angle is 90° and further wherein said first and second light transmitters are offset at an angle of 90° relative to one another.

4. An apparatus as defined in claim 1, wherein said first light transmitter comprises a first light source and said second light transmitter comprises a second light source.

5. An apparatus as defined in claim 1, further comprising a sole light source supplying with light said first and said second light transmitter.

6. An apparatus as defined in claim 1, wherein said light transmitters comprise light diodes.

7. An apparatus as defined in claim 1, wherein said light transmitters are infrared light transmitters and said light detectors are infrared light detectors.

8. An apparatus as defined in claim 1, wherein said light transmitters and light detectors are disposed relative to one another such that they enclose a space circular through which the fiber material passes.

9. An apparatus as defined in claim 1, wherein said light transmitters comprise a light source and means for parallelizing light rays emitted by the light source.

10. An apparatus as defined in claim 1, further comprising an optical means situated in front of said light detectors for concentrating the light from said light transmitters on said light detectors.

11. An apparatus as defined in claim 1, wherein said first light transmitter and said first light detector are spaced from said second light transmitter and said second light detector in a direction parallel to a travelling direction of said fiber material through the optical device.

12. An apparatus as defined in claim 1, wherein each said CCD member comprises a plurality of light detecting elements each arranged to emit an electric signal.

13. An apparatus as defined in claim 1, further comprising an electric evaluating device connected to said light detectors for receiving signals therefrom.

14. An apparatus as defined in claim 1, wherein each said light detector has a width measured transversely to a direction of travel of the fiber material; said width being greater than an expected maximum width of the fiber material measured parallel to the width of said light detector.

15. An apparatus as defined in claim 13, in combination with a carding machine; said fiber material being a sliver provided by said carding machine; further comprising an electronic regulating and control device connected to said evaluating device and said carding machine for receiving signals from said evaluating device and for applying signals to said carding machine to vary the thickness of the sliver as a function of values sensed by said optical device.

16. An apparatus as defined in claim 15, further comprising an input and output device connected to said regulating and control device.

17. A method of operating the apparatus defined in claim 1, comprising the step of cyclically interrogating the light detector in a predetermined cadence.

18. A method as defined in claim 17, further comprising the step of synchronizing said cadence with a travelling speed of said fiber material.

19. A method as defined in claim 17, wherein each said light transmitter includes a light source; further comprising the step of energizing and deenergizing each said light source in synchronism with said cadence.

20. A method of calibrating the apparatus defined in claim 1, comprising the steps of
  (a) passing a coherent fiber material of predetermined length and thickness;
  (b) determining an average volume of the fiber material;
  (c) weighing the fiber material;
  (d) determining the weight per length unit of the fiber material; and
  (e) applying the value pairs, formed of the average volume values and the weight per length unit, as a setting curve to the optical device.

* * * * *